United States Patent [19]

Calzi

[11] Patent Number: 5,204,266

[45] Date of Patent: * Apr. 20, 1993

[54] METHOD AND APPARATUS FOR LIQUID PHASE CALIBRATION OF OXYGEN AND CARBON DIOXIDE PARTIAL PRESSURE

[75] Inventor: Claudio Calzi, Milan, Italy

[73] Assignee: Instrumentation Laboratory SpA, Milan, Italy

[*] Notice: The portion of the term of this patent subsequent to Oct. 29, 2008 has been disclaimed.

[21] Appl. No.: 383,645

[22] Filed: Jul. 24, 1989

[30] Foreign Application Priority Data

Aug. 10, 1988 [IT] Italy ............... 21689 A/88

[51] Int. Cl.⁵ ............... G01N 31/00; G01N 33/50
[52] U.S. Cl. ............... 436/11; 436/68; 422/68.1; 422/81; 73/1 R
[58] Field of Search ............... 436/8–18, 436/50, 68; 252/408.1; 73/1 R; 422/68.1, 81

[56] References Cited

U.S. PATENT DOCUMENTS

| | | | |
|---|---|---|---|
| 1,919,858 | 7/1933 | Pettingill | 435/50 |
| 3,466,249 | 9/1969 | Anderson | 252/408 |
| 3,681,255 | 8/1972 | Wilfore | 252/408 |
| 3,874,850 | 4/1975 | Sorenson et al. | 23/230 B |
| 4,001,142 | 1/1977 | Turner | 252/408 |
| 4,116,336 | 9/1978 | Sorenson et al. | 206/524.8 |
| 4,163,734 | 8/1979 | Sorensen et al. | 435/18 |
| 4,369,127 | 9/1982 | Cormier et al. | 436/11 |
| 4,424,276 | 1/1984 | Clark et al. | 436/50 |
| 4,443,407 | 4/1984 | Weinberg et al. | 422/68 |
| 4,567,748 | 2/1986 | Klass et al. | 73/1 |
| 4,722,904 | 2/1988 | Feil | 436/11 |

FOREIGN PATENT DOCUMENTS 0313546 4/1989 European Pat. Off. .

OTHER PUBLICATIONS

D. C. Noonan et al, "Quality Control System for Blood pH and Gas Measurements . . . " Clin. Chem. vol. 20, No. 6, pp. 660–665 (1974).

Primary Examiner—James C. Housel
Assistant Examiner—N. Bhat
Attorney, Agent, or Firm—Testa, Hurwitz & Thibeault

[57] ABSTRACT

A pre-determined amount of solubilized reagent is reacted to release $CO_2$ in a controlled-temperature reaction vessel and a controlled-pressure area adjacent the reaction vessel.

11 Claims, 2 Drawing Sheets

METHOD AND APPARATUS FOR LIQUID PHASE CALIBRATION OF OXYGEN AND CARBON DIOXIDE PARTIAL PRESSURE

BACKGROUND OF INVENTION

The present invention relates to preparations with predetermined partial pressure of $O_2$ and $CO_2$, particularly useful for calibrating analytical instruments commonly used for measuring blood gases.

By instruments for measuring blood gases there are herein meant apparatus for diagnostic purposes adapted to measure the partial pressure of $O_2$ and $CO_2$ in venous or arterial blood, or mixtures thereof, and the pH of the same. Such instruments may also measure other parameters, and especially ions such as sodium, potassium, calcium and chloride and other analytes in whole blood such as glucose.

Instruments of this kind are normally used in hospital laboratories, intensive care units, etc., and are in particular surgical conditions indispensable, in that no other instrumental devices can fulfill the functions that they are capable of fulfilling.

On the basis of the three fundamental parameters measured, derived variables can be determined. The most significant and important derived parameter is the acid/alkali balance (an indicator of lung and renal function). Since the 1950's, many aspects of the said apparatus have evolved technologically in the interests of greater simplicity of use, automation and dependability.

Nevertheless, apparatus for measuring blood gases remain complex and delicate and, if they are to operate correctly, require frequent calibration with secondary standards. Currently provision is made for buffers of known pH for calibrating the pH channel, and mixtures of gases of known percentage for calibrating the $pO_2$ and $pCO_2$ channels. These gas mixtures ($O_2$, $CO_2$, remainder nitrogen) are generally contained in pressurized cylinders.

Certification of gas cylinder content is very costly and calls for equipment not available everywhere. Gas-mixers requiring the use of 100% $CO_2$ and ambient air have been designed and constructed to obviate this difficulty; but the problems of transportation, bulk and availability of the said cylinders remains.

Fluorocarbon emulsions, such as are described in U.S. Pat. Nos. 4,151,108, 4,163,734, 4,116,336 and 4,722,904 have been used as controls and are proposed in these patents for use as calibrants. For a variety of technical reasons, involving especially calibration of the pH electrode, fluorocarbon emulsions are not used commercially as calibrants.

The object of the present invention is to provide a solution for this problem of a kind that also simplifies the apparatus by enabling the calibrant to be maintained in the liquid phase. The apparatus can then be calibrated by means of liquid phases with pre-determined and stable partial $O_2$ and $CO_2$ pressures.

BRIEF DESCRIPTION OF THE INVENTION

The basic principle of the invention lies in generating the two species in question, $O_2$ and $CO_2$, in an aqueous (or similar) matrix whenever necessary, using physico-chemical constituents that are separate and per se stable.

If carried out in a reproducible manner within controlled physical confines, the reaction resulting from the interaction of the constituents produces and/or modifies the partial pressures of the two gases in question, thus producing liquid calibrants of known partial pressures of the two gases useful for calibrating the apparatus for measuring blood gases.

In accordance with one form of the invention, the method of preparing a substance for calibrating analytical instruments of the kind used to measure blood gases provides for: preparation of solutions of reagents adapted to generate $CO_2$, affecting in a pre-determined manner the concentration of $O_2$; sending the reagent solutions to a reaction vessel to conduct the reaction with a pre-determined amount of $CO_2$ being generated; measurement of the pressure in the area adjacent the reaction vessel and temperature in the reaction vessel; calculation of the $pCO_2$; calculation of the $PO_2$ assuming the $O_2$ concentration to be the atmospheric concentration, corrected for the effect of the reaction thereon; withdrawal of reacted solution from the reaction vessel and sending it to the analytical instrument for calibration thereof.

One preferred form of carrying the method according to the invention into practice provides that the $CO_2$ production reaction does not affect the $O_2$ concentration, so that this latter can be assumed to be that deriving from atmospheric pressure and concentration. The reagent solutions are in any case sent to reaction through a pressure equalizer apparatus (e.g. a tonometer) which brings the $pO_2$ in the said solutions into equilibrium with that determined by the atmospheric conditions in the reaction confines, indipendently of the conditions existing when the reagent solutions are prepared.

The type of control used to determine the amount of $CO_2$ produced by the reaction will depend on the type of reaction employed. In particular, the amount of $CO_2$ produced can be determined by assay of the reagents sent to reaction. In some cases when the reaction is activated by the conditions to which the reagents are subjected—typically electromagnetic radiation—the amount of $CO_2$ produced can be controlled by dosing the radiation. In other cases, the amount of $CO_2$ produced is a function of the concentration of a precursor (e.g., bicarbonate) and the proportion of the solution containing that precursor.

The apparatus according to the invention for preparing a substance for calibrating analytical instruments of the type used for measuring blood gases therefore provides for container vessels for solubilized reagents adapted to react to generate $CO_2$, respective pumps for transferring amounts of reagents to a reaction vessel through pressure equalizer means for bringing the $O_2$ pressure into equilibrium with atmospheric pressure, means for measuring temperature in the reaction vessel and pressure in the area adjacent such vessel, and a line leaving the reaction vessel for sending the reacted solution to the analytical instrument for the calibration thereof.

BRIEF DESCRIPTION OF THE DRAWINGS

The object of the invention, and its advantages over the known art, will become more apparent from an examination of the following illustrative and not limiting description of forms of embodiment thereof, with reference to the appended drawings, in which.

DETAILED DESCRIPTION OF THE INVENTION

Figure 1:
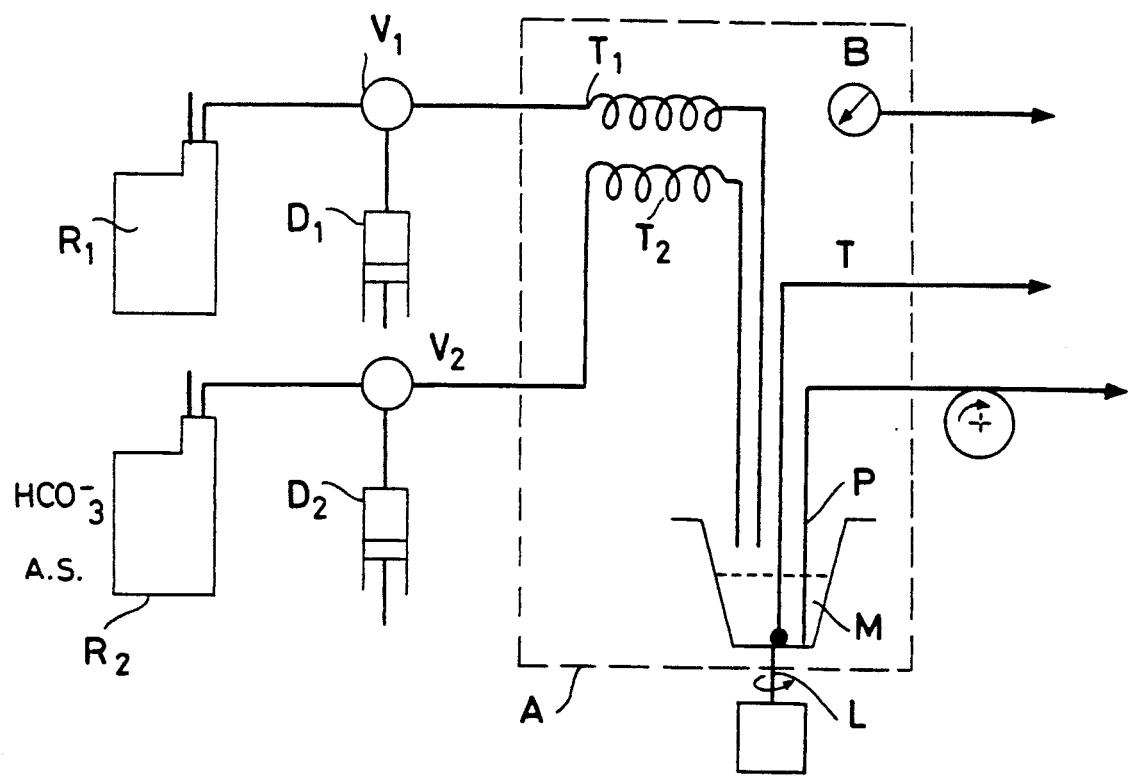
FIG. 1 is a diagrammatic illustration of the principles on which the apparatus according to the invention operates employing two reagents.

With reference to the principles illustrated in FIG. 1, these presuppose that the following reaction takes place:

$$HCO_3^- + H^+ \rightleftharpoons H_2CO_3 \rightleftharpoons H_2O + CO_2(\uparrow)$$

In FIG. 1, the apparatus comprises a first container vessel $C_1$ from which, through a valve $V_1$, a metering device $D_1$ can convey a pre-set amount of reagent $R_1$ through a tonometer $T_1$ into the reaction vessel M which has a stirrer L.

A circuit for conveying the reagent $R_2$ from the container vessel $C_2$ is formed in an entirely similar manner, the reagent being conveyed in metered amounts to the reaction vessel M through the tonometer $T_2$.

The tonometers $T_1$ and $T_2$ saturate the solutions of reagents with air in the atmospheric conditions of the area A with uniform pressure and temperature, where the pressure is detected by a barometric sensor B and the temperature by a thermometer T.

The reaction product in vessel M is then drawn off through a dip-tube P. The product solution, having known $pCO_2$, is then pumped to the analytical instrument for calibration thereof according to the present invention.

Examples of blood gas instrumentation which can be calibrated by such solutions are described in U.S. Pat. Nos. 4,361,539, 4,361,540 and 4,443,407 to Weinberg et al. and U.S. Pat. No. 4,160,714 to Sorenson et al. Minor modifications in such instruments would be needed to accomodate a liquid calibrant for the $pO_2$ and $pCO_2$ electrodes, instead of gas mixtures. Examples of such modifications are given in U.S. application Ser. No. 257,553 of Calabrese et al, filed Oct. 14, 1988 in the name of Calabrese.

When the method of the invention is carried out as above (bicarbonate/carbonic acid), the availability of two reagents $R_1$ and R, per se stable for a long period of time (24 months), can be relied upon; in particular, $R_1$ is a solution of a strong acid (H+) such as sulphuric acid, lactic acid, etc., and $R_2$ is a solution of bicarbonate (HCO3 ) in typical molar concentrations of 1.2 and 2.4 mM appropriately stabilized in the ambient air.

In general, so long as the ratios of reagents $R_1$ and $R_2$ remain constant and the resultant mixture is acidic (preferably pH 2.4 to 4.2), the $pCO_2$ of the mixture will be a positive function of the initial bicarbonate concentration. While this relationship can be empirically established without undue experimentation for any particular solutions and systems, in exemplary embodiments, bicarbonate concentrations in solution $R_2$ of 1.2 mM and 2.4 mM produced a $pCO_2$ of the mixture of 35 torr (millimeters of mercury) and 70 torr, respectively. Thus, a preferred overall range for bicarbonate concentration in reagent $R_2$ is 0.5 to 5.0 millimoles per liter, especially 1.2-2.4 mM. As evidenced by the above equilibration formula, that bicarbonate concentration can be established from raw materials which are bicarbonates, carbonates or carbon dioxide.

The devices $D_1$, $V_1$ and $D_2$, $V_2$ which enable the reagent system to be maintained in liquid phase make it possible to take off determined amounts of reagents $R_1$ and $R_2$ and to convey them through the tonometers $T_1$ and $T_2$ into the reaction vessel M. For the purposes of the invention, $T_1$ and $T_2$ are constructed from material highly permeable to ambient $O_2$, and their function is to equilibrate the two reagents $R_1$ and $R_2$ with the partial pressure of $O_2$ present at the intended reaction site; equilibrium is reached at the temperature in M, and to this end M, $T_1$ and $T_2$ are suitably coupled thermally in the area adjacent the reaction vessel indicated by A (dashed lines). Thus, knowing the solubility of the two reagents as a function of the temperature (f) T, and the temperature at A, assuming the concentration of $O_2$ in the ambient air as being the same in all atmosphere, and knowing the barometric pressure detected by B in the enclosure area A, the partial $pO_2$ in $R_1$ and $R_2$ sent to the reaction vessel M can be predicted.

The purpose of the above is to be able to avoid variabiluty based upon the temperature (and thus the moles of air dissolved) at which the container vessels $C_1$ and $C_2$ were filled with the reagents $R_1$ and $R_2$.

When, therefore, two pre-determined amounts of reagents $R_1$ and $R_2$ are introduced into the reaction vessel M and intimately mixed, the following results are produced:

$$\frac{mM/l}{HCO_3^-} = \frac{B.P. \times CO_2\%}{760 \times 100} \times \frac{\alpha \times 1000}{25.42^*} = \frac{pCO_2}{760} \times \frac{1000}{25.42}$$

$$pCO_2 = \frac{mM/l\ HCO_3^- \times 760 \times 25.42}{\alpha \times 1000} =$$

$$mM/l\ HCO_3^- \times 34.5\ 37°\ C.$$

$\alpha(f)T|°C.|$

\* $V_m$ at 37° C. and 760 mmHg

The relations (approximate) set out here indicate the production of $CO_2$ and its predictable quantification as $pCO_2$, so long as the reaction PH is between 2.4 and 4.4.

All the necessary calculations can be done independently by an appropriately programmed microprocessor, which receives the necessary information regarding the values, pre-set or detected by the control sensors, of the temperature and pressure conditions; in accordance with the indications given above, the microprocessor will be fed with the data concerning the composition, pressure and temperature of the atmosphere, the coefficients of solubility of $O_2$ and $CO_2$ in the reagents, their molar concentration, and all other variables and algorithms required for the calculation.

The reaction vessel M can be of various shapes. A truncated cone shaped, open-top reaction vessel can be adopted, as shown diagrammatically in FIG. 1. In such case, the open top of the vessel causes diffusion of $CO_2$ from the reaction product towards the air of the adjacent area A, on accounts of the gradient that is created; this difficulty can be overcome by suitably sizing the dip-tube P so that the liquid taken off to calibrate the analyzer starts to be aspirated from the bottom in quantity of about half the total available volume, and for a realatively short time. Under these conditions the amount of diffused $CO_2$ does not appreciably alter the $pCO_2$ calculated in the solution reacted in M and sent to the instrument for its calibration.

Figure 2:
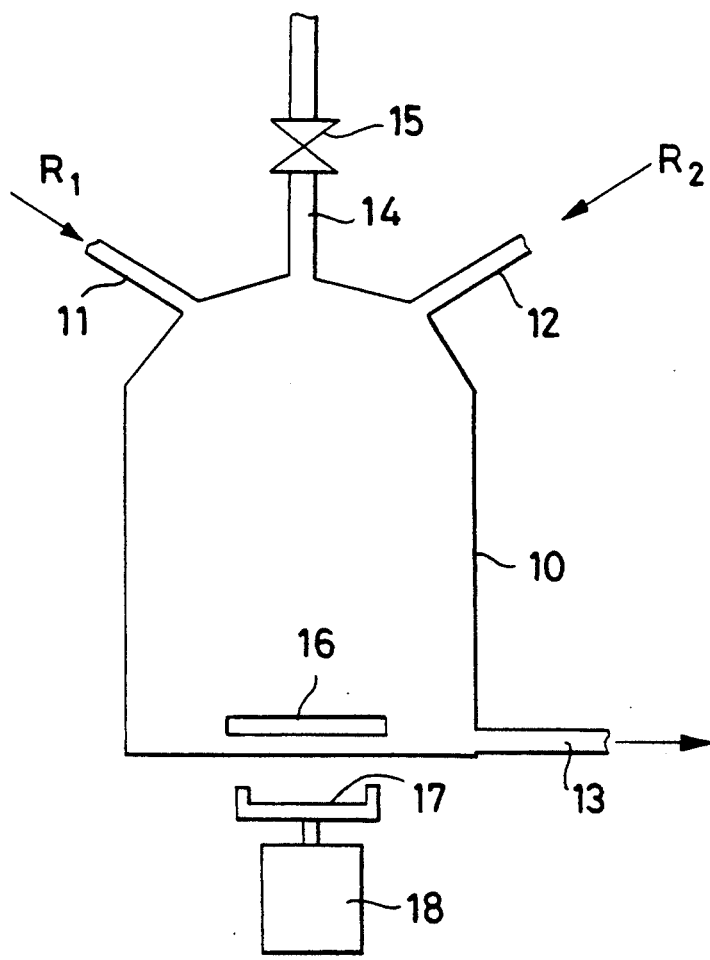
FIG. 2 is a diagrammatic illustration of a closed reaction vessel.

A closed reaction vessel, with stirrer, of the type shown in FIG. 2 can also be employed. In FIG. 2, the reaction vessel 10 can be formed by fabricating for example acrylic material. Two inlets 11 and 12 are provided, respectively for the reagents $R_1$ and $R_2$, typically the acid and the bicarbonate according to the example described. An outlet 13 conveys the reaction product to the analytical instrument for its calibration. For the vessel to be filled with the liquid phase it is preferred to provide a vent 14 communicating with atmosphere through a cutoff valve 15.

The reaction vessel has a stirrer 16 made of ferromagnetic material with its surface protected by inert material—for example thermoplastic material—which is rotated by a motor 17 by means of an electromagnetic coupling 18.

A reaction vessel of this type can be used in sistems with liquid phase integration: in this case the sensors of the apparatus that measures blood gases are to be understood as integrated as also the liquid phase pathways of the sample and auxiliary reagents.

The stirring or mixing function in this second embodiment is no longer a function of the shape of the reaction vessel, as in the first embodiment but rather of the thermoplastic stirrer. In priciple, this reaction vessel can operate in the same way as the open-top reaction vessel, even if part of the air is inevitably trapped in the reaction environment.

As mentioned heretofore, the method of the invention can also use reactions of a different nature for generating $CO_2$. In particular a direct or indirect photochemical method can be employed. BY way of illustrative and not limiting example, a direct method according to one of the following reactions can be used:

$$UO_2(C_2O_4) \xrightarrow{h\nu} UO_2{}^2 + CO_2 + H_2O + CO \quad 1)$$

2)

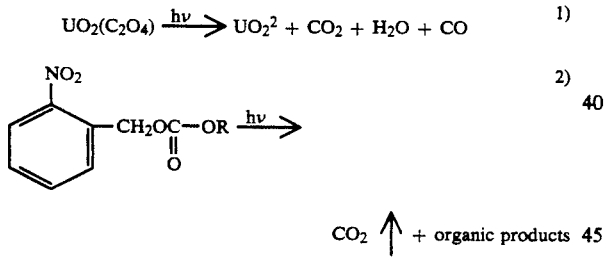

$CO_2 \uparrow$ + organic products

The method employing a photochemical generation of $CO_2$ can use an apparatus such as that described above, providing in such case for only one reagent container vessel and with a reaction vessel of configuration suitable for the reaction to be conducted.

Various methods employing such photochemical generation of carbon dioxide are described in more detail in U.S. application Ser. No. 257,553 of Calabrese and Calzi, filed Oct. 14, 1988 in the name of Calabrese, the disclosure of which is incorporated herein by reference. Further information concerning solutions used in such method is contained in U.S. application Ser. No. 305,567 of Calabrese, filed Feb. 3, 1989, the disclosure of which is also incorporated herein by reference. Two illustrative aqueous ferrioxalate solutions described in such applications are illustrated below:

| Solution 1 | |
|---|---|
| Ferric ammonium sulfate dodecahydrate | 0.20 mM |
| Potassium oxalate monohydrate | 80 mM |
| Sulfuric acid | 50 mM |

| -continued | |
|---|---|
| Solution 2 | |
| Ferric ammonium sulfate dodecahydrate | 15.0 mM |
| Potassium oxalate monohydrate | 1.5 mM |
| Sulfuric acid | 50 mM |

As illustrated in those applications, if solution 1 is equilibrated with air and then photolysed, the resultant $pCO_2$ is 35–37 torr and the resultant $pO_2$ is 15 torr or less. If Solution 2 is equilibrated with air and then photolyzed, the resultant $pCO_2$ is 73–78 torr and the resultant $pO_2$ is 168–172 torr.

Figure 3:
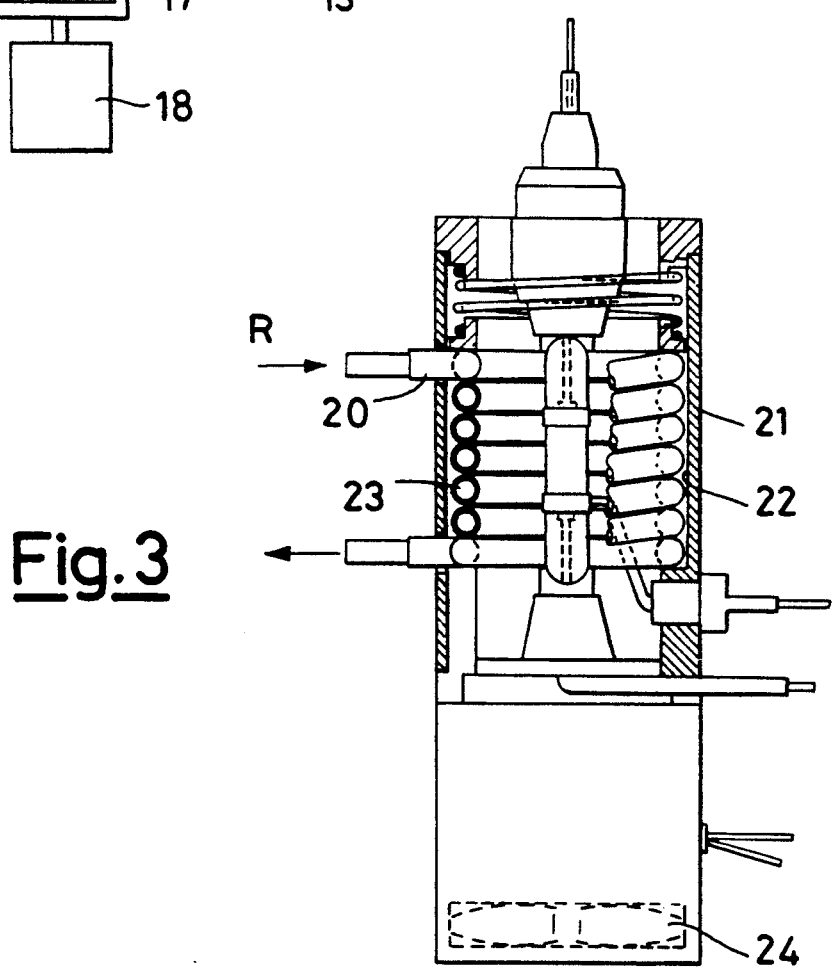
FIG. 3 illustrates a reaction vessel for carrying out the method of the invention employing one reagent only.

FIG. 3 illustrates a possible configuration of the reaction vessel when $CO_2$ is generated using the photochemical method.

In such case the reaction vessel can with advantage be given a structure permitting an as uniform as possible radiation of the reagent mass; in particular, the vessel can be given the form of a helically wound transparent tube 20, within an envelope 21 having a specular inside wall 22. The centre of the windings of the tube 20 accepts the source 23 of radiation activating the reaction, in particular ultraviolet waves, according to the reaction heretofore indicated. Low pressure xenon lamps can for example be used.

The fan shown schematically at 24 in FIG. 3 ensures a controlled temperature in the reaction vessel.

Into one end of the tube 20 there is sent the solution of the reagents for generating $CO_2$ with pre-defined $O_2$ content by reason of the passage within the relative tonometer, or similar pressure equalizer device that brings the $pO_2$ into equilibrium with atmosphere, as described above.

The solution is permitted to remain for a pre-set time in the vessel represented by the tube 20 which is radiated so as to produce a metered amount of $CO_2$.

One can operate the system to cause a correlation between the amount of emitted radiation that strikes the reagent and the amount of substance that reacts; a diagram can therefore be plotted, using the abscissa for radiation time and the ordinate for $pCO_2$, checking that after a given time (of the order of a few minutes), the $pCO_2$ line is substantially asymptotical. A family of curves can be plotted for the different concentrations of the reagent in the solution.

Alternatively, as described in U.S. application Ser. No. 257,553, one can operate the device in such a fashion that the residence time in which the reagent solution is exposed to light is sufficient for the $pCO_2$ and $pO_2$ values to approach or reach plateau levels determined by the concentration of the reagents (precursors) in the solution. This second mode of operation to somewhat preferred because it eliminates variability in results as a fraction of the output of the light source.

On expiry of the pre-set residence time of the solution in the tubular vessel 20, and thus with a known $pCO_2$ within the vessel having been attained, the solution is sent to the apparatus for measuring blood gases where it is used as calibration substance, in accordance with the objects of the invention.

In many of the embodiments described above, the $CO_2$ generation reaction does not substantially alter the $O_2$ concentration, which can therefore be considered that which the solution would have following saturation in atmospheric conditions, as explained heretofore.

All of the embodiments based upon acidification of bicarbonate have this result. Solution 2 illustrated above also produces this result upon photolysis.

Should the reaction lead to variations in $O_2$ concentration, account will be taken of such variations by accordingly correcting the concentration acquired in the pressure equalizer apparatus exemplified as tonometer.

In other embodiments of the invention, as illustrated by the photolysis of Solution 1, above, the $CO_2$ generation reaction does alter the $O_2$ concentration. As explained in U.S. application Ser. Nos. 257,553 and 305,567, the effect is to lower the $pO_2$ from atmospheric levels (150–175 torr) to levels of 25 torr or less, and especially to near zero.

The reproducibility of the cycles of the method and the reproducibility on industrial scale of the physical components of the apparatus, as obtained according to the present invention, are of essential importance. The $pCO_2$ and $pO_2$ of the liquid phase produced can thus be assigned in an exact and constant manner, making the liquid phase particularly dependable for the calibration of the apparatus measuring blood gases.

I claim:

1. A method of preparing a substance in the liquid phase having a pre-determined partial $O_2$ and $CO_2$ pressure, useful for calibrating analytical instruments of the type used to measure blood gases, which method comprises:
   a) providing a solution of reagents adapted to generate $CO_2$,
   b) affecting in a pre-determined manner the concentration of $O_2$ in the solution,
   c) conveying the reagent solution to a reaction vessel to conduct a reaction with a pre-determined amount of $CO_2$ being generated, wherein the reagent solution is conveyed to the reaction vessel through a pressure equalizer exposed to the atmosphere, to equilibrate the $pO_2$ of the reagent solution,
   d) measuring the pressure and temperature in the reaction vessel, and
   e) conveying the reacted solution from the reaction vessel to an analytical apparatus for calibration of the analytical apparatus based upon the partial $O_2$ and $CO_2$ pressures of the reacted solution.

2. A method as described in claim 1, wherein two reagent solutions are conveyed to the reaction vessel, and the amount of $CO_2$ produced by the reaction is a function of the ratio of the two solutions conveyed to the said vessel.

3. A method as described in claim 2, wherein the two reagent solutions are an acid solution and a bicarbonate solution.

4. A method as described in claim 1, wherein the $CO_2$ generation reaction does not affect the $O_2$ concentration.

5. A method as described in claim 1, wherein the reaction is conducted in an open-top reaction vessel and the reacted solution is drawn off in a partial amount with respect to the total reaction product proximally to the bottom of the vessel so that variation of $pCO_2$ due to the diffusion of $CO_2$ from solution to atmosphere is negligible.

6. A method as described in claim 1, wherein the reaction is conducted in a closed vessel.

7. An apparatus for preparing a solution having a predeterminted partial $O_2$ and $CO_2$ pressure, useful for calibrating analytical instruments of the type used for measuring blood gases, comprising:
   a. a container vessel for a reagent solution adapted to react to generate $CO_2$,
   b. pump means for transferring an amount of reagent from the container vessel into a reaction vessel through pressure equalizing means which is exposed to the atmosphere for bringing the $pO_2$ in the reagent solution into equilibrium with atmospheric $pO_2$,
   c. means for measuring temperature in the reaction vessel and pressure in the area adjacent said vessel, and
   d. withdrawing means for conveying the reacted solution into the reaction vessel to the analytical instrument for calibration thereof.

8. An apparatus as described in claim 7, wherein the pressure equalization means is a tonometer.

9. An apparatus as described in claim 7, further comprising an additional container vessel for a second reagent solution, and second pump means for transferring amounts of second reagent to the reaction vessel.

10. An apparatus as described in claim 7, wherein the reaction vessel is open-top, and wherein the withdrawing means (d) comprises a dip-tube terminating within the vessel proximal to the bottom of the vessel.

11. An apparatus as described in claim 7, wherein the reaction vessel is provided with a stirrer.

* * * * *